United States Patent
Dai et al.

(10) Patent No.: US 10,781,525 B2
(45) Date of Patent: Sep. 22, 2020

(54) ALUMINUM TRIHALIDE-NEUTRAL LIGAND IONIC LIQUIDS AND THEIR USE IN ALUMINUM DEPOSITION

(71) Applicant: UT-Battelle, LLC, Oak Ridge, TN (US)

(72) Inventors: Sheng Dai, Knoxville, TN (US); Xiao-Guang Sun, Knoxville, TN (US)

(73) Assignee: UT-Battelle, LLC, Oak Ridge, TN (US)

( * ) Notice: Subject to any disclaimer, the term of this patent is extended or adjusted under 35 U.S.C. 154(b) by 0 days.

(21) Appl. No.: 16/214,436

(22) Filed: Dec. 10, 2018

(65) Prior Publication Data
US 2019/0106799 A1    Apr. 11, 2019

Related U.S. Application Data

(63) Continuation of application No. 14/516,611, filed on Oct. 17, 2014, now Pat. No. 10,208,391.

(51) Int. Cl.
| | |
|---|---|
| C25D 3/66 | (2006.01) |
| C07C 2/22 | (2006.01) |
| C25D 3/44 | (2006.01) |
| C07C 45/56 | (2006.01) |
| C25D 5/00 | (2006.01) |

(52) U.S. Cl.
CPC ............. C25D 3/665 (2013.01); C07C 2/22 (2013.01); C07C 45/56 (2013.01); C07C 45/562 (2013.01); C07C 45/567 (2013.01); C25D 3/44 (2013.01); C25D 5/003 (2013.01)

(58) Field of Classification Search
None
See application file for complete search history.

(56) References Cited

U.S. PATENT DOCUMENTS

| | | | |
|---|---|---|---|
| 2,446,331 | A | 8/1948 | Hurley |
| 3,268,421 | A | 8/1966 | McGraw |
| 3,997,410 | A | 12/1976 | Gileadi et al. |
| 4,003,804 | A | 1/1977 | Wong |
| 4,032,413 | A | 6/1977 | Dotzer et al. |
| 4,071,415 | A | 1/1978 | Wong |
| 4,126,523 | A | 11/1978 | Wong |
| 4,145,261 | A | 3/1979 | Daenen et al. |

(Continued)

FOREIGN PATENT DOCUMENTS

| | | |
|---|---|---|
| JP | S491440 | 1/1974 |
| JP | H07180092 A | 7/1995 |
| WO | 2011109878 A1 | 9/2011 |

OTHER PUBLICATIONS

United States Office Action dated Dec. 11, 2018 issued in U.S. Appl. No. 14/516,608.

(Continued)

*Primary Examiner* — Katie L. Hammer
(74) *Attorney, Agent, or Firm* — Scully, Scott, Murphy & Presser, P.C.

(57) ABSTRACT

An ionic liquid composition comprising a complex of a trihalo aluminum (III) species with at least one organic uncharged ligand comprising a ring structure having at least three ring carbon atoms and at least one ring heteroatom selected from nitrogen and sulfur, wherein the complex is a liquid at a temperature of 100° C. or less. Methods of electroplating aluminum onto a metallic substrate using the above-described ionic liquid composition are also described.

12 Claims, 3 Drawing Sheets

(56) References Cited

U.S. PATENT DOCUMENTS

| | | |
|---|---|---|
| 4,152,220 A | 5/1979 | Wong |
| 4,226,696 A | 10/1980 | Vera |
| 4,379,030 A | 4/1983 | Daenen et al. |
| 4,721,656 A | 1/1988 | Vance et al. |
| 4,747,916 A | 5/1988 | Kato et al. |
| 5,041,194 A | 8/1991 | Mori et al. |
| 5,225,059 A | 7/1993 | Penrose |
| 5,731,101 A | 3/1998 | Sherif et al. |
| 5,827,602 A | 10/1998 | Koch et al. |
| 6,143,156 A | 11/2000 | Zhang |
| 7,235,165 B2 | 6/2007 | Lacey |
| 7,915,426 B2 | 3/2011 | Chauvin et al. |
| 8,163,834 B2 | 4/2012 | Byrne et al. |
| 8,679,576 B2 | 3/2014 | Nakai et al. |
| 8,778,163 B2 | 7/2014 | Yu et al. |
| 2001/0024691 A1 | 9/2001 | Caballero et al. |
| 2005/0102819 A1 | 5/2005 | Lee et al. |
| 2006/0211871 A1 | 9/2006 | Dai et al. |
| 2009/0301871 A1 | 12/2009 | Zappi et al. |
| 2010/0032306 A1 | 2/2010 | Abd Elhamid et al. |
| 2011/0171564 A1 | 7/2011 | Blunk et al. |
| 2011/0253543 A1 | 10/2011 | Hoshi et al. |
| 2012/0031766 A1 | 2/2012 | Inoue et al. |
| 2012/0186993 A1 | 7/2012 | Huang et al. |
| 2012/0189778 A1 | 7/2012 | Riewe et al. |
| 2013/0001092 A1 | 1/2013 | Abbott et al. |
| 2013/0284977 A1 | 10/2013 | Kunz et al. |

OTHER PUBLICATIONS

Bellavance P.L. et al., "Synthesis and Characterization of Complexes of Aluminum Halide With 2,2'-Bipyridine, 1,10-Phenanthroline, and 2,2',2"-Terpyridine in Acetonitrile", Inorganic Chemistry, (1977), 16(2):462-467.

Chen B. et al., "Highly Stretchable and Transparent Ionogels as Nonvolatile Conductors for Dielectric Elastomer Transducers", ACS Appl. Mater. Interfaces, (2014), 6:7840-7845.

Hapiot P. et al., "Electrochemical Reactivity in Room-Temperature Ionic Liquids", Chemical Reviews, (2008), 108(7):2238-2264.

Ispas A. et al., "Electrodeposition in Ionic Liquids", The Electrochemical Society Interface, (2014), pp. 47-51.

Liao Q. et al., "Electrodeposition of Aluminum from the Aluminum Chloride-1-Methyl-3-Ethylimidazolium Chloride Room Temperature Molten Salt + Benzene", J. Electrochem. Soc., (Mar. 1997), 144(3):936-943.

Markiewicz M. et al., "Potential Application of Ionic Liquids in Aluminium Production—Economical and Ecological Assessment", Physicochemical Problems of Mineral Processing , (2009), 43:73-83.

Seddon K.R., "Ionic Liquids—A Taste of the Future", Nature Materials, (Jun. 2003), 2:363-365.

Wang Q. et al., "A Promising Electrolyte of Ionic Liquids for Aluminum Deposition", 2013 AIChE Annual Meeting, Hilton San Francisco Union Square, San Francisco, CA, (Nov. 6, 2013), 1 Page.

U.S. Office Action dated Feb. 9, 2018 issued in U.S. Appl. No. 14/516,608.

United States Office Action dated Jun. 14, 2018 issued in corresponding U.S. Appl. No. 14/516,608.

ALUMINUM TRIHALIDE-NEUTRAL LIGAND IONIC LIQUIDS AND THEIR USE IN ALUMINUM DEPOSITION

CROSS REFERENCE TO RELATED APPLICATIONS

This application is a continuation of U.S. Ser. No. 14/516,611 filed Oct. 17, 2014, the entire contents of which are incorporated herein by reference.

This invention was made with government support under Prime Contract No. DE-AC05-00OR22725 awarded by the U.S. Department of Energy. The government has certain rights in the invention.

FIELD OF THE INVENTION

The present invention relates generally to aluminum-containing electrolytes useful in the electroplating of aluminum, and more particularly, to such electrolyte compositions being ionic liquids.

BACKGROUND OF THE INVENTION

Metal surface coating has played an important role in extending the life cycle of structural materials commonly used in large rugged equipment for use on land, air, and sea. Aluminum and its many versatile alloys are routinely used as surface coatings for the corrosion protection of many metals, offering both barrier and sacrificial protection. In addition, aluminum and its alloys are being considered as favorable alternatives for cadmium coatings on the protective shells of electrical connectors in military ground systems in view of the known toxic and carcinogenic nature of cadmium and hexavalent chromium materials.

Currently, there are various methods for aluminum deposition, such as hot dipping, thermal spraying, sputter deposition, vapor deposition, and electrodeposition. However, a particularly attractive method for depositing aluminum and its alloys is isothermal electrodeposition, either by tank or brush plating. Electrodeposition is an attractive technique because it generally leads to thin, economical coatings that are usually adherent and do not affect the structural and mechanical properties of the substrate. Moreover, the thickness and quality of the deposits can be controlled by adjustment of the deposition rate by tuning such experimental parameters as overvoltage, current density, electrolyte composition, and temperature.

Unfortunately, neither aluminum nor its alloys can be electrodeposited from aqueous solutions because hydrogen is evolved before aluminum can be plated. Thus, it is necessary to employ non-aqueous solvents (both molecular and ionic) for this purpose. On a commercial basis, aluminum is plated by using the well known SIGAL® process. Although known to be very effective, the SIGAL® process requires a plating bath composed of alkyl aluminum fluorides dissolved in toluene. Not surprisingly, the technique raises a number of environmental and safety objections because the alkyl aluminum compounds are pyrophoric and toxic, and the toluene solvent is flammable and can lead to volatile organic compound (VOC) emissions. The inefficiency of aqueous electroplating also makes it a major energy consumer (for example, for electrolytic hard chrome plating, only 10-20% of the power supplied is used for actual deposition; the remaining power is consumed through hydrogen generation and other losses).

More recently, aluminum-containing ionic liquids (i.e., aluminum-containing molten salts) have gained increasing prominence as substantially improved electrolytes for the deposition of aluminum. The ionic liquids possess an advantageous combination of physical properties, including non-flammability, negligible vapor pressure, high ionic conductivity, and high thermal, chemical, and electrochemical stability. Therefore, they are amenable for the electroplating of reactive elements, which is impossible using aqueous or other organic solvents. Thus far, the ionic liquids used for the electrodeposition of aluminum has focused on chloroaluminate anions, which are typically obtained by mixing anhydrous $AlCl_3$ with an organic chloride salt, such as 1-ethyl-3-methyl imidazolium chloride (EMImCl), 1-(1-butyl)pyridinium chloride (N-BPCl), or other related salt. However, because of the hygroscopic nature of $AlCl_3$ and the resulting chloroaluminate, the electroplating generally must be performed in an inert gas atmosphere, which significantly increases cost and complexity of the process. In addition, the anionic nature of the electroactive species in the ionic liquid (e.g., $Al_2Cl_7^-$) presents a significant hindrance in the ability of the electroactive species to accept electrons for aluminum deposition, which further decreases the efficiency of the process.

SUMMARY OF THE INVENTION

The instant disclosure is directed to aluminum-containing ionic liquids that overcome the problems found in ionic liquids of the art. In particular, as the instantly described ionic liquids do not include chloroaluminate ions, they are substantially less hygroscopic and more efficiently accept electrons for aluminum deposition. Thus, the instantly described ionic liquids can advantageously be used with less precaution against moisture and with greater energy efficiency. The instantly described ionic liquids achieve these improved features by being composed of an aluminum trihalide species complexed with a neutral ligand. The presence of a neutral ligand in the instant ionic liquid compositions is to be contrasted with the cationic salt ligands (e.g., imidazolium or pyridinium salt ligands) commonly used in the art.

In particular embodiments, the ionic liquid is or includes a complex of a trihalo aluminum (III) species with at least one organic uncharged ligand that includes a ring structure having at least three ring carbon atoms and at least one ring heteroatom selected from nitrogen and sulfur. The complex is generally a liquid at a temperature of 100° C. or less. In further embodiments, the ionic liquid is or includes a complex of a trihalo aluminum (III) species with at least one unsaturated heterocyclic ligand (e.g., pyridine, imidazole, pyrazine, pyrazole, pyrrole, or triazine) and/or at least one saturated heterocyclic ligand (e.g., piperidine, imidazolidine, piperazine, pyrazolidine, or pyrrolidine), wherein the unsaturated or saturated heterocyclic ligand may be unsubstituted, or may or may not include one or more alkyl substituents, particularly alkyl substituents containing at least three carbon atoms provided that the presence of the alkyl substituent does not result in a charged ligand. In still further embodiments, the ionic liquid is or includes a complex of a trihalo aluminum (III) species with an alkyl-substituted pyridine or imidazole wherein the alkyl substituent is on a ring carbon atom of the pyridine or imidazole ring. The alkyl substituent (particularly those having at least three carbon atoms) can improve the properties of the ionic liquids, particularly by decreasing their melting points and making them room temperature ionic liquids.

In another aspect, the invention is directed to a method of electroplating aluminum onto a metallic substrate by use of the above-described aluminum-containing ionic liquid. The method includes: (i) contacting the metallic substrate, in the substantial absence of water, with the above-described ionic liquid composition, wherein the above-described ionic liquid composition is in contact with an anode, and (ii) applying a voltage potential between the anode and the metallic substrate as cathode to produce a coating of aluminum on the metallic substrate while the metallic substrate is in contact with the ionic liquid composition.

DETAILED DESCRIPTION OF THE INVENTION

Figure 1:
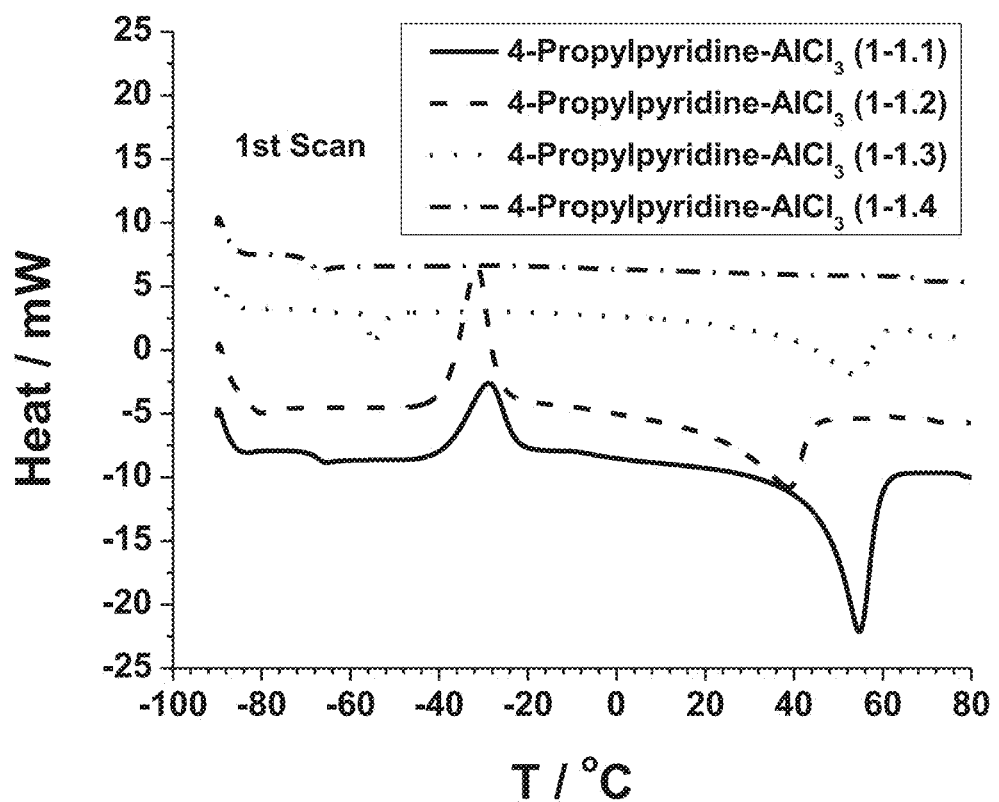
FIG. 1. Graph showing differential scanning calorimetry (DSC) curves of $AlCl_3$-4-propylpyridine ionic liquid mixtures having $AlCl_3$:4-propylpyridine ratios of 1.1:1, 1.2:1, 1.3:1, and 1.4:1.

In a first aspect, the invention is directed to an ionic liquid composition that is exclusively or includes a trihalo aluminum (III) species complexed with at least one organic uncharged (neutral) ligand (also referred to as "ligand"). The halogen atoms in the trihalo aluminum (III) species can be selected from any of the halogens, i.e., fluorine, chlorine, bromine, and iodine, which respectively correspond to aluminum fluoride ($AlF_3$), aluminum chloride ($AlCl_3$), aluminum bromide ($AlBr_3$), and aluminum iodide ($AlI_3$), and multiples thereof, such as the dimer $Al_2Cl_6$. Thus, the ionic liquids described herein can be conveniently described according to the general stoichiometric formula $AlX_3 \cdot L_n$, where X is a halogen atom, L is an organic uncharged ligand, and n is an integer of at least 1, typically 1, 2, or 3. Molecules of solvation (i.e., adducts) may or may not also be included in the formula. Multiples of the foregoing general formula (e.g., $Al_2X_6 \cdot L_{2n}$) are also embraced by the general formula. The term "complex" or "complexed", as used herein, indicates a bonding interaction between the neutral organic ligand and the aluminum ion. The association between the aluminum ion and ligand is typically a dative covalent interaction, generally between the electron-deficient aluminum ion and electron-donating heteroatom in the ligand. As the ligand considered herein is uncharged, there is no ionic bonding between the aluminum ion and the ligand. There is, however, an ionic association between the aluminum ion and the halide atoms, which provides the ionic character of the composition.

The organic uncharged ligand particularly considered herein is or includes a ring structure having at least three ring carbon atoms and at least one ring heteroatom selected from nitrogen and sulfur. In different embodiments, the ring heteroatoms may be selected from only nitrogen atoms, or only sulfur atoms, or a combination of nitrogen and sulfur atoms, or a combination of nitrogen and oxygen atoms, or a combination of sulfur and oxygen atoms. The ring structure may be unsaturated (e.g., aliphatic or aromatic) or saturated. The ring structures generally contain a total of five, six, or seven ring atoms (i.e., five-, six-, or seven-membered rings), at least three of which are ring carbon atoms and at least one of which is a heteroatom. Generally, the ring structure includes one, two, or three ring heteroatoms.

Some examples of five-membered unsaturated rings containing at least one ring nitrogen atom include pyrrole, imidazole, pyrazole, oxazole, isoxazole, thiazole, and the triazole rings (i.e., 1,2,3-triazole and 1,2,4-triazole). Some examples of six-membered unsaturated rings containing at least one ring nitrogen atom include pyridine, pyrazine, pyrimidine, pyridazine, 1,3,5-triazine, and oxazine rings. Some examples of seven-membered unsaturated rings containing at least one ring nitrogen atom include azepine and the diazepine rings (e.g., 2-diazepine, 3-diazepine, and 1,4-diazepine).

Some examples of five-membered saturated rings containing at least one ring nitrogen atom include pyrrolidine, imidazolidine, oxazolidine, and thiazolidine rings. Some examples of six-membered saturated rings containing at least one ring nitrogen atom include piperidine, piperazine, morpholine, and thiomorpholine rings. Some examples of seven-membered saturated rings containing at least one ring nitrogen atom include azepane and diazepane rings.

Some examples of unsaturated rings containing at least one ring sulfur atom include thiophene, thiazole, isothiazole, and thiadiazole rings. Some examples of saturated rings containing at least one ring sulfur atom include tetrahydrothiophene and thiopyran rings.

The ring structure containing the at least one heteroatom may or may not also be fused to another ring, thereby resulting in a fused ring structure. Some examples of fused ring structures include indole, purine, quinoline (benzopyridine), isoquinoline, benzimidazole, benzoxazole, benzothiazole, benzoxazoline, benzothiophene, benzoxazine, and phenoxazine.

In some embodiments, the ring structure of the uncharged ligand includes at least one alkyl substituent (i.e., alkyl group) containing at least one carbon atom. The alkyl substituent can improve the properties of the ionic liquids, particularly by decreasing their melting points, and preferably making them room temperature ionic liquids. In different embodiments, the alkyl group can include precisely or at least one, two, three, four, five, six, seven, eight, nine, ten, eleven, or twelve carbon atoms, or a number of carbon atoms within a range bounded by any two of the foregoing numbers. The alkyl group can be straight-chained or branched. Some examples of straight-chained alkyl groups include methyl, ethyl, n-propyl, n-butyl, n-pentyl, n-hexyl, n-heptyl, n-octyl, n-nonyl, n-decyl, n-undecyl, and n-dodecyl groups. Some examples of branched alkyl groups include isopropyl, isobutyl, see-butyl, t-butyl, isopentyl, neopentyl, 2-methyl pent-1-yl, 3-methylpent-1-yl, isohexyl, isoheptyl, and isooctyl groups.

In other embodiments, the ring structure of the uncharged ligand includes at least one alkenyl substituent alkenyl group) containing at least two carbon atoms and the presence of at least one carbon-carbon double bond. The alkenyl substituent can also improve the properties of the ionic liquids, particularly by decreasing their melting points, and preferably making them room temperature ionic liquids. In different embodiments, the alkenyl group can include precisely or at least two, three, four, five, six, seven, eight, nine, ten, eleven, or twelve carbon atoms, or a number of carbon atoms within a range bounded by any two of the foregoing numbers. The alkenyl group can be straight-chained or branched. Some examples of straight-chained alkenyl groups include vinyl, propen-1-yl (allyl), 3-buten-1-yl ($CH_2=CH-CH_2-CH_2-$), 2-buten-1-yl ($CH_2-CH=CH-CH_2-$), butadienyl, 4-penten-1-yl, 3-penten-1-yl, 2-penten-1-yl, 5-hexen-1-yl, 6-hepten-1-yl, and the like. Some examples of branched alkenyl groups include propen-2-yl, 1-buten-3-yl $CH_3$), 1-buten-2-yl ($CH_2=C.-CH_2-CH_3$), 1-penten-4-yl, 1-penten-3-yl, 2-penten-4-yl, 2-penten-3-yl, and 1,4-pentadien-3-yl.

In some embodiments, the at least one alkyl or alkenyl group attached to the ring structure is composed of only carbon and hydrogen atoms. In other embodiments, the alkyl or alkenyl group may include one or more heteroatoms, such as one or more selected from oxygen, nitrogen, sulfur, and halogen atoms. A particular example of an alkyl group substituted with at least one heteroatom is an alkyl group containing at least one oxygen atom, e.g., a hydroxy group (OH), or ether group (—O—) as found in the alkoxides (i.e., —OR, where R is an alkyl group with or without further heteroatom substitution) or groups of the general formula —$(CH_2)_s$—$(O-CH_2CH_2)_t$H, where s is 0 or an integer from 1 to 12 and t is 0 or an integer from 1-12. A protic group, such as OH, should not be present in the ionic liquid if it becomes deprotonated by other groups in the ionic liquid or by another component in contact with the ionic liquid. In some embodiments, the alkyl group may be a partially or completely fluorinated alkyl group, such as $CF_3$, or $CF_2CF_3$, or a fluorinated sulfone, such as —$SO_2F$ or —$SO_2CF_3$.

The at least one alkyl or alkenyl substituent can be included on the ring structure provided that it does not result in a charged ligand. For example, in the case of an unsaturated ring, the alkyl or alkenyl substituent must not be located on a ring nitrogen atom if the nitrogen atom is part of an unsaturated bond, since this would result in a positively charged ring nitrogen atom (i.e., the alkyl or alkenyl substituent can only be located on a ring carbon atom in that case). If the ring nitrogen atom is not part of an unsaturated bond (either in an unsaturated or saturated ring), then the ring nitrogen atom can bear a single alkyl or alkenyl substituent while remaining uncharged, as long as the ring nitrogen atom is not part a fused side of a fused ring system. The alkyl or alkenyl substituent must not be located on a ring sulfur atom since this would result in a positively charged ring sulfur atom.

In particular embodiments, the ionic liquid is or includes an alkyl-substituted or alkenyl-substituted pyridine or imidazole ring, wherein the alkyl or alkenyl substituent is on a ring carbon atom of the pyridine or imidazole ring. The alkyl-substituted pyridine ligand can be, for example, a 2-alkyl-pyridine, 3-alkyl-pyridine, 4-alkyl-pyridine, 2,3-dialkyl-pyridine, 2,4-dialkyl-pyridine, 3,4-dialkyl-pyridine, 2,3,4-trialkyl-pyridine, 3,4,5-trialkyl-pyridine, or 2,3,5-trialkyl-pyridine, wherein it is understood that the number designating the alkyl group is relative to the location of the ring nitrogen atom, where the ring nitrogen atom is designated as position 1 (thus, a 4-alkyl-pyridine contains the alkyl group in a position directly opposite from the ring nitrogen atom in the pyridine ring). In similar fashion, the alkyl-substituted imidazole ligand can be, for example, a 2-alkylimidazole, 4-alkylimidazole, 2,4-dialkylimidazole, 4,5-dialkylimidazole, or 2,4,5-trialkylimidazole, wherein it is understood that the number designating the alkyl group is relative to the location of the ring nitrogen atoms, which occupy positions 1 and 3 on the imidazole ring. The alkyl group in any of the above exemplary alkyl-substituted pyridine or imidazole ligands can be replaced with an alkenyl group to provide an equal number of exemplary alkenyl-substituted pyridine and imidazole ligands. The ring may also include a combination of alkyl and alkenyl groups. In some embodiments, the alkyl-substituted ring contains no substituent other than one or more alkyl and/or alkenyl substituents, i.e., remaining positions on the ring are occupied by hydrogen atoms.

The ionic liquid described herein is typically a liquid at room temperature (e.g., 15, 18, 20, 22, 25, or 30° C.) or lower. However, in some embodiments, the ionic liquid may not be a liquid at room temperature, but becomes a liquid at a higher temperature than 30° C. if it is used at an elevated temperature that melts the compound to be an ionic liquid. Thus, in some embodiments, the ionic liquid may have a melting point of up to or less than 100, 90, 80, 70, 60, 50, 40, or 35° C. In other embodiments, the ionic liquid may be a liquid at a temperature of or less than 100, 90, 80, 70, 60, 50, 40, or 35° C. In other embodiments, the ionic liquid is a liquid at or below 10, 5, 0, −10, −20, −30, or −40° C. The term "liquid", as used herein, indicates an ability of the substance to readily flow, typically no more than about 1,000 centipoise (1,000 cP). In different embodiments, the viscosity of the ionic liquid is up to or less than, for example, 1,000, 800, 700, 600, 500, 400, 300, 200, 100, 50, 25, 10, 5, or 1 cP, or a viscosity within a range bounded by any two of these values. The term "about", as used herein, generally indicates no more than ±10, ±5, ±2, or ±1% from an indicated value.

The ionic liquids described above are generally prepared by combining and mixing an aluminum trihalide (e.g., $AlCl_3$) and the organic neutral ligand in the liquid state in a molar ratio that produces a composition that behaves as an ionic liquid at a desired temperature, such as room temperature. In some embodiments, the mixture is heated to ensure dissolution of the aluminum trihalide in the organic neutral ligand. In particular embodiments, the ratio of aluminum trihalide to organic neutral ligand is precisely or about, for example, 0.5:1, 0.6:1, 0.7:1, 0.8:1, 0.9:1, 1:1, 1.1:1, 1.2:1, 1.3:1, 1.4:1, 1.5:1, 1.6:1, 1.7:1, 1.8:1, 1.9:1, or 2:1, or a ratio within a range bounded by any two of the foregoing values.

In another aspect, the instant disclosure is directed to methods for electroplating aluminum onto a metallic substrate by use of any of the ionic liquids described above. In the method, the metallic substrate is contacted with the ionic liquid while the ionic liquid is in contact with an anode, and a suitable voltage potential is established between the anode and the metallic substrate polarized as cathode. In a typical embodiment, the substrate is at least partly or completely submerged into an electroplating bath containing the ionic liquid and a suitable voltage potential is established between the anode and the metallic substrate as cathode.

The metallic substrate can have any composition for which deposition of aluminum may be desired. The metallic substrate may include, for example, one or more metals selected from titanium, tantalum, iron, cobalt, nickel, copper, and zinc, and thus, may be a substantially pure metal or a binary, ternary, or higher alloy. In particular embodiments, the metallic substrate is iron, or an iron-containing alloy, such as a steel.

The anode can be any of the anodes well known in the art for electroplating aluminum. In one embodiment, the anode is an aluminum anode. In another embodiment, the anode is an inert anode, such as a porous or non-porous graphite, titanium-containing, tantalum-containing, or platinum-containing anode.

In one embodiment, the electroplating bath (i.e., electroplating solution) contains the ionic liquid in the substantial or complete absence of a solvent. In another embodiment, the electroplating bath contains the ionic liquid in admixture with one or more solvents. The solvent may function, for example, to help solubilize other components in the electroplating solution (e.g., an electrolyte salt), improve wettability, or improve qualities of the aluminum deposit. The one or more solvents can be selected from any of the organic and inorganic solvents known in the art, provided that the solvent or solvent mixture does not adversely react or interact with the ionic liquid or the plating process. The solvent or solvent mixture should be completely miscible with the ionic liquid and any other components that may be included in the electroplating bath.

The organic solvent can be ionic or non-ionic. In the case of an ionic solvent, the ionic solvent can be any of the ionic liquids of the art, i.e., an ionic liquid outside of the ionic liquids described herein. In the case of a non-ionic solvent, the non-ionic solvent can be, for example, a hydrocarbon, alcohol, ketone, carbonate, sulfone, siloxane, ether, nitrile, sulfoxide, or amide solvent, or a mixture thereof. Some examples of hydrocarbon solvents include hexanes, cyclohexane, benzene, toluene, decalin, and xylenes, or halogenated versions of hydrocarbons, e.g., methylene chloride, trichloroethylene, or perchlorethylene. Some examples of alcohol solvents include methanol, ethanol, n-propanol, isopropanol, n-butanol, and isobutanol, and the dials, such as ethylene glycol, methylene glycol, and triethylene glycol. Some examples of ketone solvents include acetone and 2-butanone. Some examples of carbonate solvents include propylene carbonate (PC), ethylene carbonate (EC), butylene carbonate (BC), dimethyl carbonate (DMC), and fluorocarbonate solvents (e.g., fluoroethylene carbonate and trifluoromethyl propylene carbonate). Some examples of sulfone solvents include methyl sulfone, ethyl methyl sulfone, methyl phenyl sulfone, methyl isopropyl sulfone (IMPS), propyl sulfone, butyl sulfone, tetramethylene sulfone (sulfolane), and phenyl vinyl sulfone. Some examples of siloxane solvents include hexamethyldisiloxane (HMDS), 1,3-divinyltetramethyldisiloxane, the polysiloxanes, and polysiloxane-polyoxyalkylene derivatives. Some examples of ether solvents include 1,2-dimethoxyethane, 1,2-diethoxyethane, 1,3-dioxolane, tetrahydrofuran, 2-methyltetrahydrofuran, tetrahydropyran, diglyme, triglyme, 1,3-dioxolane, and the fluorinated ethers (e.g., mono-, di-, tri-, tetra-, penta-, hexa- and per-fluoro derivatives of any of the foregoing ethers). Some examples of nitrile solvents include acetonitrile, propionitrile, and butyronitrille. Some examples of sulfoxide solvents include dimethyl sulfoxide, ethyl methyl sulfoxide, diethyl sulfoxide, methyl propyl sulfoxide, and ethyl propyl sulfoxide. Some examples of amide solvents include formamide, N,N-dimethylformamide, N,N-diethylformamide, acetamide, N,N-dimethylacetamide, N,N-diethylacetamide, gamma-butyrolactam, and N-methylpyrrolidone. Other organic solvents include hexamethylphosphoramide (HMPA) and 1,3-dimethyl-3,4,5,6-tetrahydro-2(1H)-pyrimidinone (DMPU). In the case of an inorganic solvent, the inorganic solvent is other than water, such as carbon disulfide or supercritical carbon dioxide. In some embodiments, any one or more of the above classes or specific types of solvents are excluded from the electroplating solution.

If a solvent is included, the one or more ionic liquids described herein can be included in any suitable amount, typically at least 10 wt % by weight of solvent and ionic liquid described herein. In different embodiments, the ionic liquid described herein is included in an amount of precisely, about, at least, or above, for example, 10, 15, 20, 25, 30, 35, 40, 45, 50, 60, 70, 80, 90, 95, 98, or 100 wt % by weight of the ionic liquid plus solvent, or an amount within a range bounded by any two of the foregoing exemplary values.

In some embodiments, one or more salts of an alkali or alkaline earth metal is included in the electroplating solution to increase the conductivity of the plating solution or to improve aspects of the aluminum deposit. The salt should be completely dissolved in the electroplating solution at the temperature employed for electroplating. The salt can be, for example, a halide of an alkali or alkaline earth metal. Some examples of alkali halides include lithium chloride, lithium bromide, sodium fluoride, sodium chloride, sodium bromide, potassium chloride, and potassium bromide. Some examples of alkaline earth halides include magnesium chloride, magnesium bromide, and calcium chloride. The salt can be included in any desired amount to suitably adjust the conductivity of the bath or other aspects of the process. In some embodiments, the salt is included in an amount of 0.1, 0.5, 1, 2, 5, 10, 15, or 20 wt % by weight of the electroplating solution, or in an amount within a range bounded by any two of the foregoing values.

The electroplating process can employ any of the conditions commonly used in the art of aluminum electroplating, provided that the conditions are suitably adjusted and modified, if necessary, to accommodate the ionic liquid described herein. The conditions can be as disclosed, for example, in U.S. Pat. Nos. 4,003,804, 4,071,415, 4,126,523, 4,152,220, 4,379,030, and 5,041,194, the contents of which are herein incorporated by reference in their entirety.

In some embodiments, the electroplating process is conducted in air without alteration of the atmosphere. In other embodiments, the electroplating process is conducted under a modified atmosphere, which can be partially or completely composed of an inert gas. The inert gas may be, for example, nitrogen or argon. The use of an inert gas may be helpful in preventing or lessening exposure of the ionic liquid to moisture and oxygen.

In some embodiments, the electroplating process is conducted with the electroplating solution being at or below room temperature, e.g., a temperature of about, up to, or less than 15, 20, 25, or 30° C. In other embodiments, the electroplating process is conducted with the electroplating solution being at an elevated temperature, such as a temperature of about, at least, or above 40, 50, 60, 70, 80, 90, 100, 110, or 120° C. In other embodiments, the electroplating process is conducted with the electroplating solution being at temperature within a range bounded by any two of the foregoing exemplary temperatures.

The electroplating process may use direct or pulse current. Any suitable current density may also be used, such as a current density of at least 0.01, 0.05, 0.1, 0.5, or 1 A/dm$^2$ and up to 2, 5, 10, 15, 20, 25, 30, 40, or 50 A/dm$^2$. The electroplating time may be suitably varied and used in conjunction with a particular current density and temperature to achieve a desired thickness of the aluminum coating. The electroplating time may be, for example, 1, 5, 10, 20, 30, 40, 50, 60, 90, or 120 minutes depending on the current density and temperature to achieve a desired thickness. The thickness of the aluminum coating may be precisely, about, at least, above, up to, or less than, for example, 1, 2, 5, 10, 20, 30, 40, 50, 60, 70, 80, 90, 100, 150, 200, 250, or 300 microns, or a thickness within a range bounded by any two of the foregoing values.

Examples have been set forth below for the purpose of illustration and to describe certain specific embodiments of the invention. However, the scope of this invention is not to be in any way limited by the examples set forth herein.

EXAMPLES

Preparation of Ionic Liquids Based on Aluminum Chloride and 4-Propylpyridine

In this experiment, 4-propylpyridine was used as a neutral ligand to prepare complexes with aluminum chloride at different $AlCl_3$ to ligand ratios. In each case, $AlCl_3$ was added to a specific amount of 4-propypyridine very slowly and under stirring. During the initial part of the addition, the $AlCl_3$ became dissolved into the 4-propylpyridine. However, as $AlCl_3$ continued to be added, the solution changed to a gel at room temperature. The gel became a liquid when warmed. After cooling the liquid back down to room temperature, the mixtures with $AlCl_3$:4-propylpyridine ratios of 1.0:1, 1.1:1, 1.2:1 and 1.3:1 remained as a liquid for one or two days in a supercooled state, after which they changed to a gel. However, the mixture having a $AlCl_3$:4-propylpyridine ratio of 1.4:1 remained as a liquid, while the mixture having a $AlCl_3$:4-propylpyridine ratio of 1.5:1 showed white precipitation after a few days at room temperature.

Analysis of the Ionic Liquids Based on Aluminum Chloride and 4-Propylpyridine

To check the thermal properties, differential scanning calorimetry (DSC) was conducted for the complexes with $AlCl_3$:4-propylpyridine ratios of 1.1:1, 1.2:1, 1.3:1 and 1.4:1, with the plotted results shown in FIG. 1 and summary provided in Table 1 below. The mixtures having ratios of 1:1, 1.2:1 and 1.3:1 exhibit crystallization points and melting points, while the mixture having a ratio of 1.4:1 exhibits only a glass transition temperature.

TABLE 1

Summary of thermal properties for $AlCl_3$-4-propylpyridine mixtures

| $AlCl_3$:4-propylpyridine | $T_g$ (° C.) | $T_{cry}$ (° C.) | $T_m$ (° C.) |
|---|---|---|---|
| 1.1:1 | −69 | −39 | 44 |
| 1.2:1 | −82.5 | −39 | 24.5 |
| 1.3:1[a] | −66 | −18 | 41.5 |
| 1.4:1 | −69.5 | | |

[a] Estimated by second scan during heating

Figure 2:
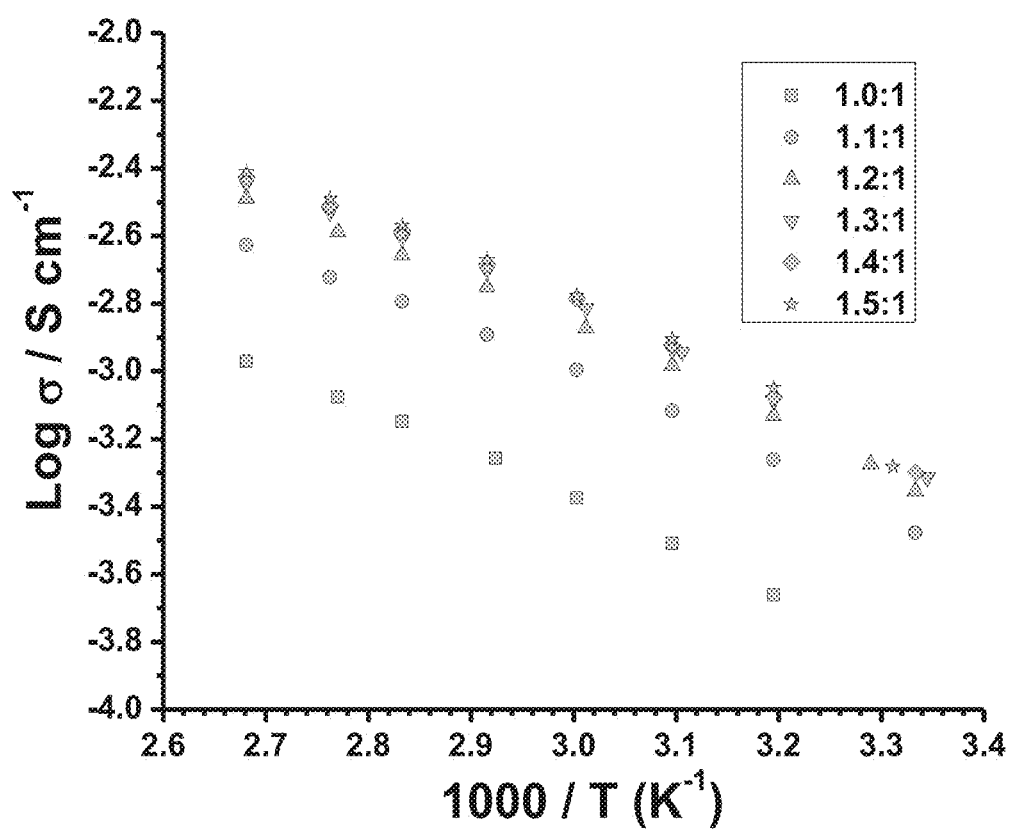
FIG. 2. Graph showing temperature dependence of the ionic conductivities of $AlCl_3$-4-propylpyridine ionic liquid mixtures having $AlCl_3$:4-propylpyridine ratios of 1:1, 1.1:1, 1.2:1, 1.3:1, 1.4:1, and 1.5:1.

FIG. 2 shows the ionic conductivities of the mixtures measured during the cooling down process. As shown in FIG. 2, the 1:1 complex has the lowest ionic conductivity among all the mixtures. When the $AlCl_3$:4-propylpyridine ratio is increased to 1.1:1, the ionic conductivity is increased by a half-order magnitude. With further increasing of the ratio, the ionic conductivity increases slowly, with ratios of 1.3:1, 1.4:1 and 1.5:1 being almost the same.

Figure 3:
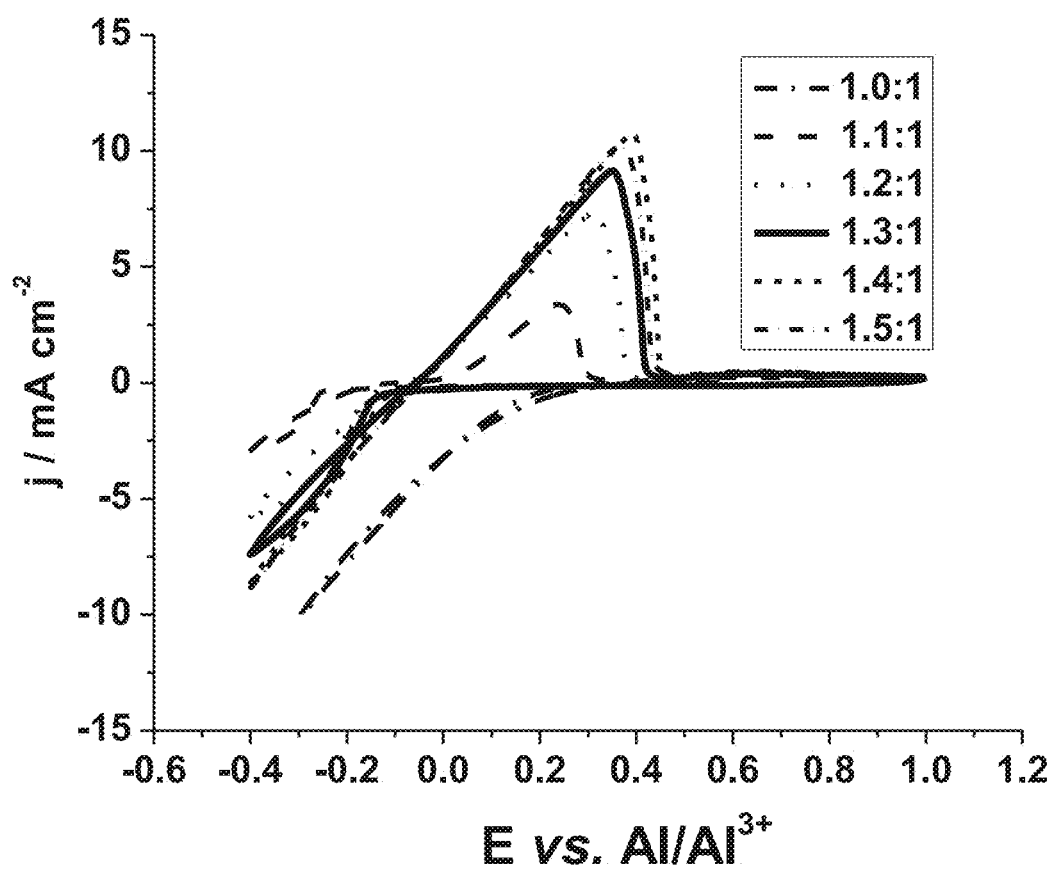
FIG. 3. Graph showing cyclic voltammograms of freshly prepared $AlCl_3$-4-propylpyridine mixtures on a Pt working electrode (0.5 mm diameter) at room temperature (the 1:1 mixture was scanned at 80° C.). Aluminum (Al) coiled wire and Al wire was used as the counter electrode and the reference electrode, respectively. The scan rate was 100 mV/s.

To confirm utility of the mixtures for electroplating aluminum, cyclic voltammetries (CVs) were measured on a Pt working electrode at a scan rate of 100 mV/s with coiled aluminum wire and aluminum wire as counter electrode and reference electrode, respectively. The results are provided in FIG. 3. As shown in FIG. 3, no reversible aluminum deposition/stripping process was observed for the mixture of 1:1, but for the other mixtures, a reversible aluminum deposition/stripping process was observed. The CV results in FIG. 3 also shows that the deposition/stripping current increases with increasing ratios, which is consistent with the increase of ionic conductivity shown in FIG. 2. The CV results in FIG. 3 also show that the overpotential decreased with increasing mixing ratio, which is beneficial in the industrial electroplating of aluminum.

The reversible aluminum deposition/stripping observed for the mixtures $AlCl_3$-4-propylpyridine establishes that the neutral ligand-complexed aluminum trihalides described herein are electroactive and can be used for electroplating aluminum. Moreover, substituent groups on the ligand can be incorporated into the ligand and adjusted in size (e.g., alkyl chain length) to suitably modify the properties of the ionic liquid, the processing conditions, and characteristics of the aluminum coat.

While there have been shown and described what are at present considered the preferred embodiments of the invention, those skilled in the art may make various changes and modifications which remain within the scope of the invention defined by the appended claims.

What is claimed is:

1. An ionic liquid composition comprising a complex of a trihalo aluminum (III) species with at least one organic uncharged ligand selected from alkyl-substituted pyridine, alkenyl-substituted pyridine, alkyl-substituted imidazole, alkenyl-substituted imidazole, alkyl-substituted thiophene, and alkenyl-substituted thiophene, wherein the alkyl or alkenyl contains at least three carbon atoms, wherein said complex is a liquid at a temperature of 100° C. or less.

2. The ionic liquid composition of claim 1, wherein said complex is a liquid at a temperature of 50° C. or less.

3. The ionic liquid composition of claim 1, wherein said complex is a liquid at a temperature of 30° C. or less.

4. The ionic liquid composition of claim 1, wherein the ionic liquid composition contains said complex in liquid form in the substantial absence of an organic or inorganic solvent.

5. A method of electroplating aluminum onto a metallic substrate, the method comprising:
   (i) contacting said metallic substrate, in the substantial absence of water, with an ionic liquid composition comprising a complex of a trihalo aluminum (III) species with at least one organic uncharged ligand selected from alkyl-substituted pyridine, alkenyl-substituted pyridine, alkyl-substituted imidazole, alkenyl-substituted imidazole, alkyl-substituted thiophene, and alkenyl-substituted thiophene, wherein the alkyl or alkenyl contains at least three carbon atoms, wherein said complex is a liquid at a temperature of 100° C. or less, and wherein said ionic liquid composition is in contact with an anode, and
   (ii) applying a voltage potential between the anode and said metallic substrate as cathode to produce a coating of aluminum on said metallic substrate while the metallic substrate is in contact with the ionic liquid composition.

6. The method of claim 5, wherein said metallic substrate is comprised of at least one metal selected from titanium, tantalum, iron, cobalt, nickel, copper, and zinc.

7. The method of claim 5, wherein the ionic liquid composition contains said complex in liquid form in the substantial absence of an organic or inorganic solvent.

8. The method of claim 7, wherein step (ii) is conducted at a temperature of up to 100° C., at which temperature said complex is a liquid.

9. The method of claim 7, wherein step (ii) is conducted at a temperature of up to 50° C., at which temperature said complex is a liquid.

10. The method of claim 7, wherein step (ii) is conducted at a temperature of up to 30° C., at which temperature said complex is a liquid.

11. The ionic liquid composition of claim 1, wherein the organic uncharged ligand is 4-alkyl-pyridine or 4-alkenyl-pyridine.

12. The ionic liquid composition of claim 1, wherein the organic uncharged ligand is 4-propyl-pyridine.

* * * * *